US009101311B2

(12) United States Patent
Mao et al.

(10) Patent No.: US 9,101,311 B2
(45) Date of Patent: Aug. 11, 2015

(54) CARDS FOR SAMPLE STORAGE AND DELIVERY COMPRISING SINTERED POROUS PLASTIC

(71) Applicants: Guoqiang Mao, Peachtree City, GA (US); James P. Wingo, Peachtree City, GA (US)

(72) Inventors: Guoqiang Mao, Peachtree City, GA (US); James P. Wingo, Peachtree City, GA (US)

(73) Assignee: POREX CORPORATION, Fairburn, GA (US)

( * ) Notice: Subject to any disclaimer, the term of this patent is extended or adjusted under 35 U.S.C. 154(b) by 11 days.

(21) Appl. No.: 14/254,550

(22) Filed: Apr. 16, 2014

(65) Prior Publication Data

US 2014/0234891 A1    Aug. 21, 2014

Related U.S. Application Data

(63) Continuation of application No. 14/007,486, filed as application No. PCT/US2012/034061 on Apr. 18, 2012.

(60) Provisional application No. 61/476,837, filed on Apr. 19, 2011.

(51) Int. Cl.
    *B01L 3/00*    (2006.01)
    *A61B 5/15*    (2006.01)
    *A61B 10/00*    (2006.01)
    *G01N 1/02*    (2006.01)
    *A61B 5/151*    (2006.01)
    *G01N 33/52*    (2006.01)

(52) U.S. Cl.
    CPC ....... *A61B 5/150343* (2013.01); *A61B 5/15101* (2013.01); *A61B 10/0045* (2013.01); *B01L 3/50* (2013.01); *B01L 3/508* (2013.01); *B01L 3/5023* (2013.01); *B01L 3/5029* (2013.01); *B01L 3/5088* (2013.01); *G01N 1/02* (2013.01); *A61B 10/0096* (2013.01); *B01L 3/5085* (2013.01); *B01L 2200/12* (2013.01); *B01L 2300/0861* (2013.01); *G01N 33/521* (2013.01); *G01N 2001/028* (2013.01); *Y10T 29/49826* (2015.01); *Y10T 436/25* (2015.01)

(58) Field of Classification Search
    None
    See application file for complete search history.

(56) References Cited

U.S. PATENT DOCUMENTS 5,116,576 A * 5/1992 Stanley .................. 422/413
5,496,542 A   3/1996 Hauschild
(Continued)

FOREIGN PATENT DOCUMENTS

EP    0392377    10/1990
EP    795600    9/1997
(Continued)

OTHER PUBLICATIONS

PCT/US2012/034061, "International Preliminary Report on Patentability", Oct. 31, 2013, 10 pages.
(Continued)

*Primary Examiner* — Jennifer Wecker
(74) *Attorney, Agent, or Firm* — Kilpatrick Townsend & Stockton LLP

(57) ABSTRACT

This application discloses cards comprising sintered porous plastic which may be employed in liquid sample collection, storage, transport and/or delivery to an analytical device. Sintered porous plastic materials provide a unique porous structure, an inert substrate, precise liquid holding capability, are quick drying, and easy to cut and handle.

19 Claims, 6 Drawing Sheets

(56) References Cited

U.S. PATENT DOCUMENTS

| | | | |
|---|---|---|---|
| 5,516,487 A * | 5/1996 | Rosenthal et al. | 422/420 |
| 5,756,126 A | 5/1998 | Burgoyne | |
| 5,760,315 A | 6/1998 | Verheijden et al. | |
| 5,807,527 A | 9/1998 | Burgoyne | |
| 5,985,327 A * | 11/1999 | Burgoyne | 424/488 |
| 6,168,922 B1 * | 1/2001 | Harvey et al. | 435/6.16 |
| 6,379,318 B1 | 4/2002 | Nishimura et al. | |
| 6,447,804 B1 | 9/2002 | Burgoyne | |
| 6,627,226 B2 | 9/2003 | Burgoyne et al. | |
| 6,746,841 B1 | 6/2004 | Fomovskaia et al. | |
| 6,869,572 B1 | 3/2005 | Kopaciewicz et al. | |
| 6,958,392 B2 | 10/2005 | Fomovskaia et al. | |
| 7,405,083 B2 | 7/2008 | Chen | |
| 2001/0000149 A1 | 4/2001 | Smith et al. | |
| 2002/0015947 A1 * | 2/2002 | Charlton et al. | 435/5 |
| 2002/0037269 A1 * | 3/2002 | Liotta et al. | 424/78.08 |
| 2002/0045270 A1 | 4/2002 | Schurenberg et al. | |
| 2003/0096424 A1 * | 5/2003 | Mao et al. | 436/169 |
| 2003/0098121 A1 * | 5/2003 | Moya | 156/275.1 |
| 2003/0134100 A1 * | 7/2003 | Mao et al. | 428/304.4 |
| 2004/0161365 A1 * | 8/2004 | Siu Yu | 422/56 |
| 2006/0105402 A1 * | 5/2006 | Rott et al. | 435/7.21 |
| 2007/0176093 A1 * | 8/2007 | Kukla et al. | 250/288 |
| 2007/0259445 A1 * | 11/2007 | Cerda | 436/173 |
| 2008/0078256 A1 * | 4/2008 | Christie et al. | 73/863.23 |
| 2008/0138823 A1 * | 6/2008 | Staab | 435/6 |
| 2008/0199363 A1 * | 8/2008 | Mao | 422/100 |
| 2014/0017693 A1 | 1/2014 | Mao | |

FOREIGN PATENT DOCUMENTS

| | | |
|---|---|---|
| EP | 2128617 | 12/2009 |
| JP | 63221244 | 9/1988 |
| JP | 03293311 | 12/1991 |
| JP | 04012243 | 1/1992 |
| JP | 06503875 | 4/1994 |
| JP | 07167779 | 7/1995 |
| JP | 08224078 | 9/1996 |
| JP | 09243639 | 9/1997 |
| JP | 10104226 | 4/1998 |
| JP | 11271218 | 10/1999 |
| JP | 2000199761 | 7/2000 |
| JP | 2001083163 | 3/2001 |
| JP | 2001281117 | 10/2001 |
| JP | 2003083974 | 3/2003 |
| JP | 2004184100 | 7/2004 |
| JP | 2004530136 | 9/2004 |
| JP | 2004340971 | 12/2004 |
| JP | 2005055316 | 3/2005 |
| JP | 2005091007 | 4/2005 |
| JP | 2006508340 | 3/2006 |
| JP | 2007508552 | 4/2007 |
| JP | 2007192673 | 8/2007 |
| JP | 2007529001 | 10/2007 |
| JP | 2009539115 | 11/2009 |
| WO | 0014532 | 3/2000 |
| WO | 02097392 | 12/2002 |
| WO | 2005018803 | 3/2005 |
| WO | WO 2005018803 A1 * | 3/2005 |
| WO | 2010127059 | 11/2010 |
| WO | 2012145390 | 10/2012 |
| WO | 2012145390 | 10/2013 |

OTHER PUBLICATIONS

PCT/US2012/034061, "International Search Report and Written Opinion", Sep. 10, 2012, 16 pages.

U.S. Appl. No. 14/007,486, Non-Final Office Action mailed Jul. 23, 2014, 27 pages.

Japanese Patent Application No. 2014-506512, Office Action mailed on Jun. 24, 2014, 11 pages.

Office Action, European Patent Application No. 12719157.5, mailed Nov. 3, 2014, 6 pgs.

* cited by examiner

CARDS FOR SAMPLE STORAGE AND DELIVERY COMPRISING SINTERED POROUS PLASTIC

CROSS REFERENCE TO RELATED APPLICATIONS

This application is a continuation of U.S. Serial No. 14/007,486 titled "Cards for Sample Storage and Delivery Comprising Sintered Porous Plastic" filed Sep. 25, 2013, which application is a U.S. national phase patent application under 35 U.S.C. 371 of International Patent Application No. PCT/US2012/034061 entitled "Cards for Sample Storage and Delivery Comprising Sintered Porous Plastic" filed Apr. 18, 2012, which claims benefit of priority of U.S. patent application No. 61/476,837 filed on Apr. 19, 2011. These applications are incorporated herein by reference in their entireties.

FIELD OF THE INVENTION

The present invention provides cards comprising sintered porous plastic which may be employed in liquid sample collection, storage, transport and/or delivery to an analytical device.

BACKGROUND

Sample cards found in the prior art are made of cellulose and are used to collect blood samples. Such cards include the Whatman FTA cards known to one of ordinary skill in the art as DMPK-A, DMPK-B and DMPK-C cards. Some of these cards may provide problems with increased background noise or interference in an analytical method such as mass spectroscopy due to interfering substances in the card. These cards also display long drying times after application of a liquid sample. Cellulose based products in certain cases may not be compatible with analytes of interest for measurement. Accordingly, there is a need for new media that can overcome the shortfalls of current sample card media and provide reliable, fast and broad range of compatibilities for sample collection, storage and subsequent analysis.

SUMMARY

This application solves the problems inherent in prior art cards and discloses cards comprising sintered porous plastic which may be employed in liquid sample collection, storage, transport and/or delivery to an analytical device. This application also discloses methods of making and using these cards.

These cards comprise sintered porous plastic which is used to receive, transport or store the liquid sample. These regions of sintered porous plastic to which a sample is applied are called sample receiving spots. Optionally, the sample receiving spots may be linked through channels to sample storage spots. These channels and sample storage spots are also comprised of sintered porous plastic.

Sample receiving spots are located or configured in a card. When present, the channels and sample storage spots are also located or configured in the card.

The regions of the card other than the sample receiving spot, the channel and the sample storage spot comprise materials which may be the same as or different from the sintered porous plastic. These regions may be sintered porous plastic, paper, cardboard, glass, and transparent or non-transparent solid non-porous plastic.

Sintered porous plastic sample receiving spots comprise a sintered porous matrix made by fusing individual plastic particles together in a sintering process to form the sintered porous matrix. These sintered porous plastic sample receiving spots configured in a card provide a unique porous structure, an inert substrate, precise liquid holding capability, dry quickly and are easy to cut and handle.

The card contains one or more liquid sample receiving spots for receipt of a liquid sample. In one embodiment, a portion of the spot may be later removed for subsequent processing and analysis of the sample contained in the spot. In another embodiment, the entire sample receiving spot may be later removed from the card for subsequent processing and analysis of the sample contained in the spot. The perimeter of the sample receiving spot may be configured for easy removal from the card.

The sintered porous matrix in the liquid sample receiving spot, in the channel and in the sample storage spot each optionally comprises functional additives. Functional additives include, but not limited to the following: polyelectrolytes, C-18, C-8 or C-4 modified silica, silica gel, ion exchange material, controlled porous glass (CPG), solid phase extraction (SPE) media, cell lysis reagents, protein denaturing additives, chemicals that denature or de-activate proteins and/or lyse cells, anti-oxidants, chemicals that preserve the analyte to be measured in the sample, enzyme inhibitors, antimicrobials, color change indicators, chelating agents, surfactants, DNA stabilizing agents, a weak acid, such as Tris(hydroxymethyl)aminomethane (TRIS), a chaotropic agent, an anti-coagulant, or a combination thereof.

DETAILED DESCRIPTION

Figure 1:
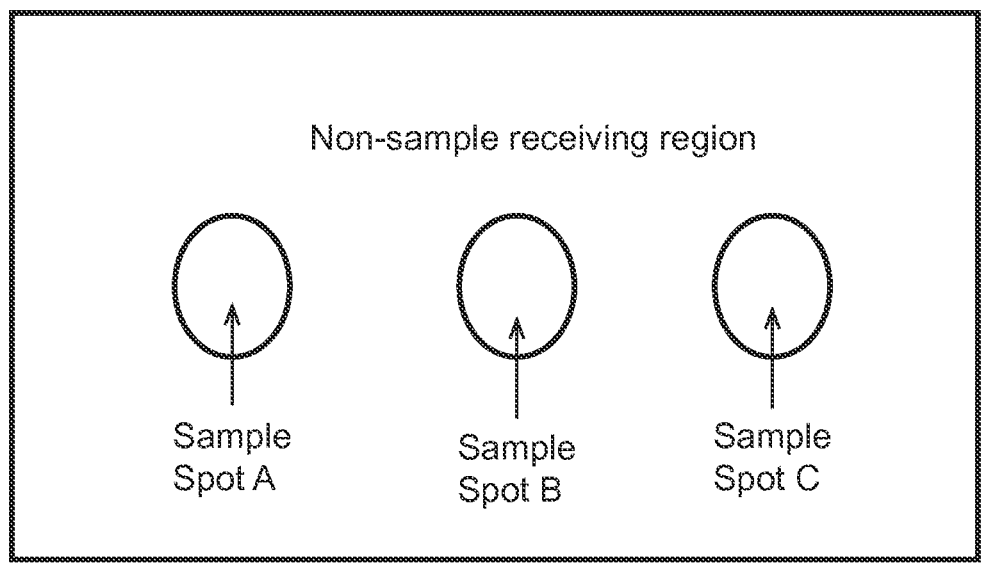
FIG. 1. Schematic representation of a sample card showing three sample spot receiving regions A, B, and C comprised of sintered porous plastic, surrounded by a region of the card that does not receive a sample.
Figure 2:
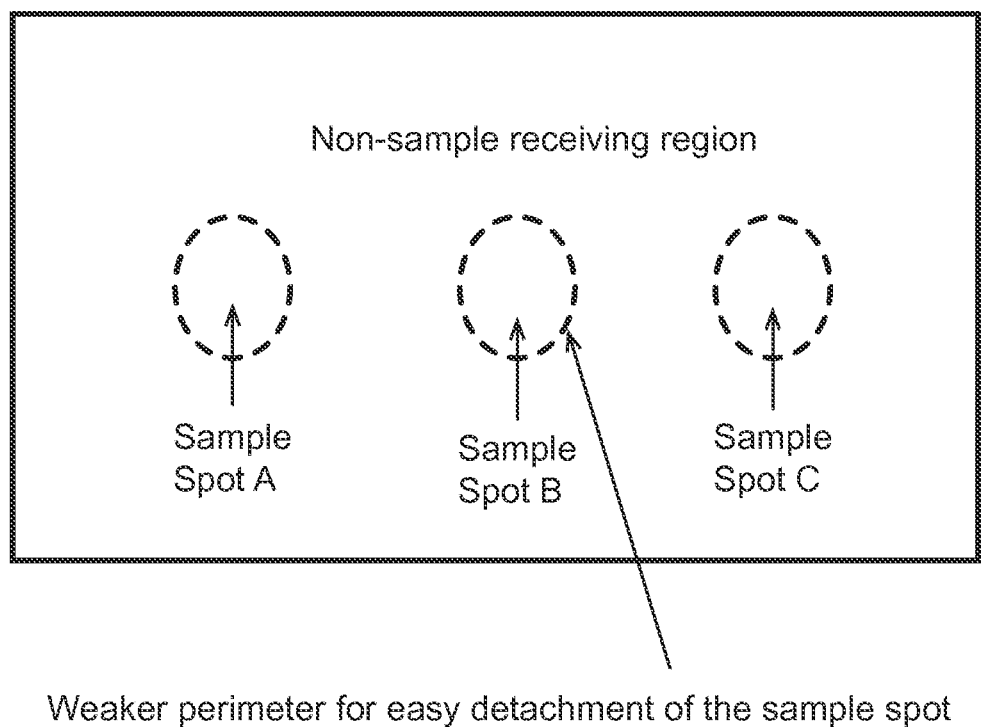
FIG. 2. Schematic representation of a sample card showing three sample spot receiving regions A, B, and C comprised of sintered porous plastic, surrounded by a region of the card that does not receive a sample. The perimeter of each sample spot comprises weak edges for easy detachment of the sample receiving spot from the card.
Figure 3:
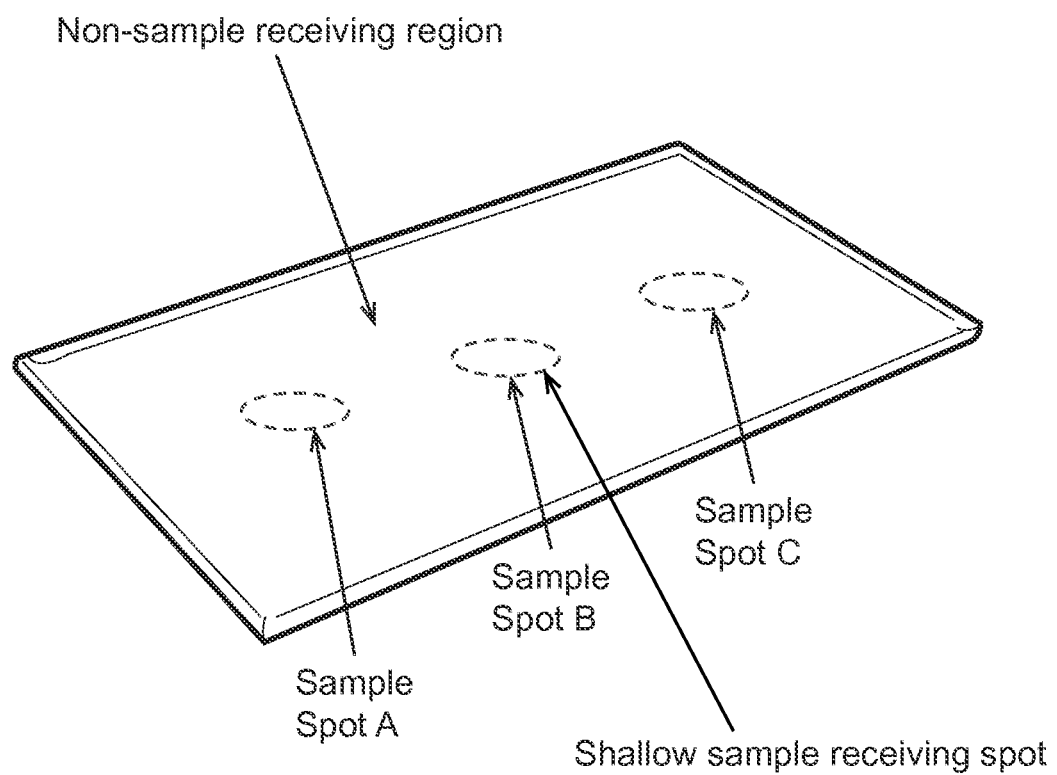
FIG. 3. Schematic representation of a sample card showing three sample spot receiving regions A, B, and C comprised of sintered porous plastic, surrounded by a region of the card that does not receive a sample. Each sample spot receiving region comprises a shallow region as the thickness of the card in the sample spot receiving region is less than the surrounding region of the card that does not receive a sample.
Figure 4:
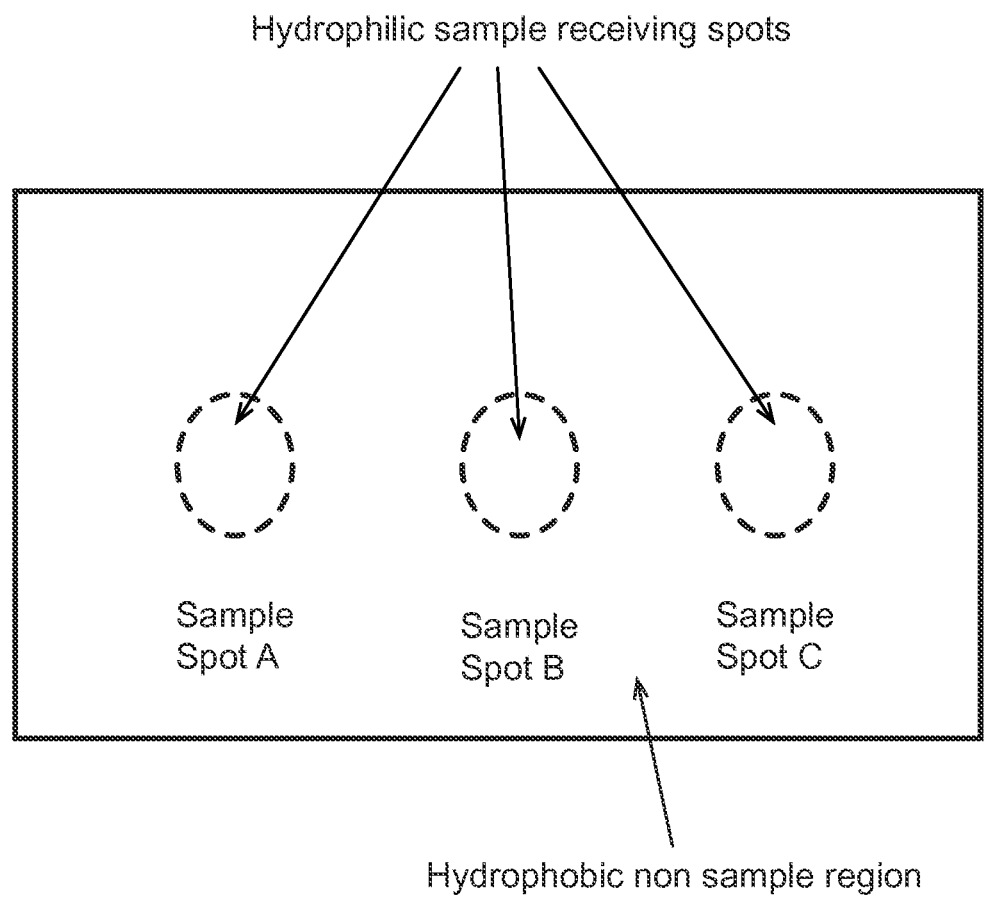
FIG. 4. Schematic representation of a sample card showing three sample spot receiving regions A, B, and C comprised of sintered porous plastic, surrounded by a region of the card that does not receive a sample. Each sample spot receiving region is hydrophilic while the surrounding region of the card that does not receive a sample is hydrophobic.

This application discloses cards comprising sintered porous plastic which may be employed in liquid sample collection, storage, transport and/or delivery to an analytical device. This application also discloses methods of making and using these cards.

These cards comprise sintered porous plastic which is used to receive, transport or store the sample. These regions of sintered porous plastic to which a sample is applied are called sample receiving spots. Optionally, the sample receiving spots may be linked through channels to sample storage spots. These channels and sample storage spots are also comprised of sintered porous plastic.

Sample receiving spots are located or configured in a card. When present, the channels and sample storage spots are also located or configured in the card.

The regions of the card other than the sample receiving spot, the channel and the sample storage spot comprise materials which may be the same as or different from the sintered porous plastic. These regions may be sintered porous plastic, paper, cardboard, glass, and transparent or non-transparent solid non-porous plastic.

Sintered porous plastic sample receiving spots comprise a sintered porous matrix made by fusing individual plastic particles together in a sintering process to form the sintered porous matrix. These sintered porous plastic sample receiving spots configured in a card provide a unique porous structure, an inert substrate, precise liquid holding capability, dry quickly and are easy to cut and handle.

The card contains one or more sample receiving spots for receipt of a liquid sample. In one embodiment, a portion of the spot may be later removed for subsequent processing and analysis of the sample contained in the spot. In another embodiment, the entire sample receiving spot may be later removed from the card for subsequent processing and analysis of the sample contained in the spot. The perimeter of the sample receiving spot may be configured for easy removal from the card.

Each of the sintered porous matrix in the sample receiving spot, in the channel and in the sample storage spot optionally comprises functional additives. Functional additives include, but not limited to the following: polyelectrolytes, C-18, C-8 or C-4 modified silica, silica gel, ion exchange material, controlled porous glass (CPG), solid phase extraction (SPE) media, cell lysis reagents, protein denaturing additives, chemicals that denature or de-activate proteins and/or lyse cells, anti-oxidants, chemicals that preserve the analyte to be measured in the sample, enzyme inhibitors, antimicrobials, color change indicators, chelating agents, surfactants, DNA stabilizing agents, a weak acid, such as Tris(hydroxymethyl) aminomethane (TRIS), a chaotropic agent, an anti-coagulant, or a combination thereof.

Cards
Composition and Properties of Cards

Cards are comprised of one or more sample receiving spots comprising a sintered porous plastic matrix and regions that do not receive a sample. The cards may be any shape including circular, oblong, polygonal, triangular, trapezoidal, rectangular or square.
Sample Receiving Spots The sintered porous matrix in the sample receiving spot, the channel or in the sample storage spot may be made from a variety of plastics such as polyethylene. Polyethylenes (PE) which may be employed include but are not limited to high density polyethylene (HDPE), low density polyethylene (LDPE), or ultra high molecular weight polyethylene (UHMWPE), or a blend thereof. The sintered porous matrix may also be made from polypropylene (PP), polyvinylidene fluoride (PVDF), polystyrene, polyamides, polyacrylates, polyacrylic nitrile (PAN), ethylene-vinyl acetate (EVA), polyesters, polycarbonates, or polytetrafluoroethylene (PTFE), or a blend thereof. In one embodiment the plastic is HDPE. In other embodiment the plastic is UHMWPE, PP, polyamides, or polyacrylic nitrile or a blend thereof. The sintered porous matrix may also be made from a blend of any of the plastics disclosed in this paragraph. In other embodiments when PP and PE are combined, PP may be present in a range of from about 100% to about 0% and PE may be present in a range of from about 0 to about 100% (100% to 0%:0% to 100% wt:wt %). When PE is combined with other polymers, the PE is present in at least about 50% (wt %).

In addition to plastic, the sintered porous matrix may also comprise hydrophilic polymers, such as celluloses, polyvinyl alcohol (PVA), polyethylene glycol (PEG) or polyvinylpyrrolidone (PVP).

The sintered porous matrix has a porosity of from about 20% to about 80%, from about 25% to about 70%, from about 30% to about 60%, or from about 30% to about 50%. The sintered porous matrix has a pore size of from about 1 µm to about 200 µm, from about 10 µm to about 100 µm, or from about 20 µm to about 60 µm. The sample receiving spots can have a thickness of from about 100 microns (µm) to about 5 mm, or from about 200 µm to about 3 mm, or from about 0.5 mm to about 2 mm.

Cards can contain one or more sample receiving spots. The number of sample receiving spots per card and their diameters and thicknesses are selected based on a variety of factors such as the volume capacity of an individual spot, the suspected analyte concentration within the sample applied to the sample receiving spot and the assay sensitivity, and the sample volume to be applied to an individual spot. The sample receiving spot may be any shape including circular, oblong, polygonal, triangular, trapezoidal, rectangular or square.

A sample receiving spot may be hydrophobic or hydrophilic, and this property is chosen depending on the sample to be applied to the sample receiving spot. In one embodiment, the sample receiving spots are hydrophilic so that hydrophilic samples may be absorbed into the card. Hydrophilic sample receiving spots are preferred for use with blood samples. Hydrophobic sample receiving spots may be desirable if the sample contains surfactant or has a surface tension of the liquid sample less than about 40 dynes/cm.

The amount of absorbed sample is controlled by the cross sectional area, thickness and pore volume of the sample receiving spot in the card. In one embodiment, the sample is absorbed into the sample receiving spot by capillary force.

The sample capacity of a sample receiving spot on a card may be from about 0.1 µl to about 500 µl, from about 1 µl to about 250 µl, from about 2 µl to about 225 µl, from about 3 µl to about 200 µl, from about 5 µl to about 150 µl, from about 10 µl to about 100 µl, from about 5 µl to about 50 µl, from about 10 µl to about 40 µl, or from about 10 µl to about 30 µl. The pore volume of a sample receiving spot on a card may be greater than about 1 µl or less than about 1000 µl, or any value between about 1 µl and about 1000 µl, or from about 0.1 µl to about 500 µl, from about 1 µl to about 250 µl, from about 2 µl to about 225 µl, from about 3 µl to about 200 µl, from about 5 µl to about 150 µl, from about 10 µl to about 100 µl, from about 5 µl to about 50 µl, from about 10 µl to about 40 µl, or from about 10 µl to about 30 µl.

Regions of the Card that do not Receive Sample

The regions of the card that do not receive sample may be made from plastic, paper, cardboard, glass or other materials When the regions of the card that do not receive sample are made from plastic, they may be porous or non-porous in different embodiments. A variety of plastics may be used, such as polyethylene. Polyethylenes (PE) which may be employed include but are not limited to high density polyethylene (HDPE), low density polyethylene (LDPE), or ultra high molecular weight polyethylene (UHMWPE), or a blend thereof. Other plastics which may be used include polypropylene (PP), polyvinylidene fluoride (PVDF), polystyrene, polyamides, polyacrylates, polyacrylic nitrile (PAN), ethylene-vinyl acetate (EVA), polyesters, polycarbonates, or polytetrafluoroethylene (PTFE), or a blend thereof. In one embodiment the plastic is HDPE. In other embodiment the plastic is UHMWPE, PP, polyamides, or polyacrylic nitrile or a blend thereof. A blend of any of the plastics disclosed in this paragraph may also be employed. In other embodiments when PP and PE are combined, PP may be present in a range of from about 100% to about 0% and PE may be present in a range of from about 0 to about 100% (100% to 0%:0% to 100% wt:wt %). When PE is combined with other polymers, the PE is present in at least about 50% (wt %).

When these regions of the card that do not receive sample are comprised of sintered porous plastic, the porosity is from about 20% to about 80%, from about 25% to about 70%, from about 30% to about 60%, or from about 30% to about 50%. The pore size is of from about 1 µm to about 200 µm, from about 10 µm to about 100 µm, or from about 20 µm to about 60 µm. These regions of the card that do not receive sample can have a thickness of from about 100 µm to about 5 mm, or from about 200 µm to about 3 mm, or from about 0.5 mm to about 2 mm.

These regions of the card that do not receive sample may be hydrophobic or hydrophilic.

Functional Additives

Sample receiving spots comprising a sintered porous plastic matrix as well as the regions of the card that do not receive a sample may contain functional additives. Functional additives include but are not limited to the following: polyelectrolytes, C-18, C-8 or C-4 modified silica, silica gel, ion exchange material, controlled porous glass (CPG), solid phase extraction (SPE) media, cell lysis reagents, protein denaturing additives, chemicals that denature or de-activate proteins and/or lyse cells, anti-oxidants, chemicals that preserve the analyte to be measured in the sample, enzyme inhibitors, antimicrobials, and color change indicators, etc. Functional additives are generally located in the sample receiving spot. Functional additives are added to the sample receiving spots during the sintering process or after the sintering process using solution treatment, depending on the sensitivity and stability of the functional additive to sintering conditions, as known to one of ordinary skill in the art.

Functional additives also include but are not limited to chelating agents, such as ethylene diaminetetraacetic acid (EDTA), surfactants, such as anionic surfactant, cationic surfactant or non-ionic surfactant, DNA stabilizing agents, such as uric acid or urate salt, or a weak acid, such as Tris(hydroxymethyl)aminomethane (TRIS). Functional additives also include but are not limited to a chaotropic agent, such as urea, thiourea, guanidinium chloride, or lithium perchlorate. Cards may also contain an anti-coagulant, such as heparin, citrate and/or chelating agents. A surfactant can be an anionic surfactant, for example sodium dodecylsulfate (SDS), sodium dodecyl sulfate (SDS), sodium dodecyl benzenesulfonate, sodium lauryl sarcosinate, sodium di-bis-ethylhexyl sulfosuccinate, sodium lauryl sulfoacetate or sodium N-methyl-N-oleoyltaurate, a cationic surfactant, such as cetyltrimethylammonium bromide (CTAB) or lauryl dimethyl benzyl-ammonium chloride, a non-ionic surfactant, such as nonyl phenoxypolyethoxylethanol (NP-40), Tween-20, Triton-100 or a zwitterionic surfactant, such as 3-[(3-Cholamidopropyl)dimethylammonio]-1-propanesulfonate. Fluorosurfactants may also be used, such as Zonyl® fluorosurfactant from DuPont. Other surfactants may be employed as known to one of ordinary skill in the art.

Sample cards, including sample receiving spots as well as other regions of the card, may also be coated with layers of polyelectrolytes, such as polyethyleneimine which may be applied in solution form. Polyelectrolyte coatings may optionally be combined with surfactants and/or an anticoagulant such as heparin.

The sintered porous plastic matrix in the sample receiving spot, the channel or the sample storage spot may contain color change indicators that dissolve upon contact with liquid and indicate the extent of sample application. In one embodiment, the sample receiving spot changes color upon contact with a liquid sample. Such color change indicators are disclosed in US 2008/0199363. In one embodiment, the sample receiving spot changes from white to another color provided by the dye the dissolves upon contact with liquid, indicating the extent of sample application. In another embodiment, the sample receiving spot may be colored and a dye dissolves upon contact with liquid to modify or reduce the coloration, indicating the extent of sample application. These color change indicators are particles that are located in the sintered porous plastic matrix. These particles of color change indicators are added to the particles of plastic and mixed before sintering to form the sintered porous plastic matrix in the area of the sample receiving spot. In another embodiment, these particles of color change indicators are added to the particles of plastic and mixed before sintering to form the sintered porous plastic matrix in the area of the sample receiving spot and also in the sintered porous plastic matrix in the region of the card outside of the sample receiving spot in order to indicate that the sample volume has exceeded the sample receiving spot. These particles of color change indicators retain particulate characteristics in the sintered porous plastic matrix as they have a higher melting temperature than the plastic particles. When particles of color change indicators are employed, the sintering temperature is chosen to sinter plastic particles but not to melt the dye particles.

Manufacture of Cards

Cards may be made with different methods depending on the composition of the card. In one embodiment, when cards are made entirely of sintered porous plastic, cards are made by placing plastic particles in a mold of desired shape and then sintering using heat to form the card. Sintering temperatures for specific plastics are known to one of ordinary skill in the art. The sample receiving spots and non-sample receiving regions on the card may have the same chemical composition or a different chemical composition. In this embodiment, sample receiving spots are used to collect, store, transport and/or deliver the samples and non-sample receiving regions are used to make the card in the desired shapes and to provide a surface for labeling the card. Based on the design, cards may have variety of shapes and arrangements.

In one embodiment, plastic cards are molded. The molding and sintering conditions to make sintered porous cards depends on the polymer. One of ordinary skill in the art is familiar with the temperatures and pressures that are appropriate for specific polymers.

A representative method of making a single component card follows. Plastic particles, in some embodiments, are sintered at a temperature ranging from about 200° F. to about 700° F. In other embodiments, plastic particles are sintered at a temperature ranging from about 300° F. to about 500° F. The sintering temperature, according to embodiments of the present invention, is dependent upon and selected according to the identity of the plastic particles as known to one of ordinary skill in the art.

Plastic particles, in some embodiments, are sintered for a time period ranging from about 30 seconds to about 30 minutes. In other embodiments, plastic particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of plastic particles is performed under ambient pressure (1 atm). In other embodiments sintering of plastic particles is performed under pressures greater than ambient pressure.

A representative method of making a dual component card with different sample receiving spots and non-sample receiving regions follows. The first plastic particle mix is deposited in a sample receiving spot portion of a mold. The second plastic mix is deposited in the non-sample receiving portion of the mold adjacent to the first portion of the mold. Next the first plastic particle mix and second plastic particle mix are sintered to form the cards containing a sampling region and non sampling region with different properties.

First plastic particles and second plastic particles, in some embodiments, have average sizes ranging from about 1 µm to about 1 mm. In another embodiment, first plastic particles and second plastic particles have average sizes ranging from about 10 µm to about 900 µm, from about 50 µm to about 500 µm, or from about 100 µm to about 400 µm. In a further embodiment, first plastic particles and second plastic particles have average sizes ranging from about 200 µm to about 300 µm. In some embodiments, first plastic particles and second plastic particles have average sizes less than about 1 µm or greater than about 1 mm. Sizes of first plastic particles and second plastic particles, in some embodiments, are selected independently.

First plastic particles and second plastic particles, in some embodiments, are sintered at a temperature ranging from about 200° F. to about 700° F. In some embodiments, first plastic particles and second plastic particles are sintered at a temperature ranging from about 300° F. to about 500° F. The sintering temperature, according to embodiments of the present invention, is dependent upon and selected according to the identity of the first plastic particles and second plastic particles as known to one of ordinary skill in the art.

First plastic particles and second plastic particles, in some embodiments, are sintered for a time period ranging from about 30 seconds to about 30 minutes. In other embodiments, first plastic particles and second plastic particles are sintered for a time period ranging from about 1 minute to about 15 minutes or from about 5 minutes to about 10 minutes. In some embodiments, the sintering process comprises heating, soaking, and/or cooking cycles. Moreover, in some embodiments, sintering of first plastic particles and second plastic particles is conducted under ambient pressure (1 atm). In other embodiments sintering of first plastic particles and second plastic particles is conducted under pressures greater than ambient pressure.

A polymeric material, such as a card, produced by sintering first plastic particles and second plastic particles, in some embodiments of the present invention, can comprise a sample receiving spot and a non-sample receiving region, the sample receiving spot comprising the sintered first plastic particles optionally with other additives, and the non-sample receiving region comprising the sintered second plastic particles. The shape of the mold can be any desired shape allowing for the facile and single-step production.

In another embodiment, the sintered porous plastic sample card can be sintered into a sheet form on a flat heating moving belt. The heating temperature and belt moving speed depend on the polymers as known to one of ordinary skill in the art. The sintered porous plastic sheet then can be die cut to the desired size and shape. The sheet can be also thermally formed into desired shapes.

In one embodiment, cards are manufactured such that the perimeter of the sample receiving spot is somewhat thinner or weaker than the sample receiving spot or the plastic material outside the perimeter. This perimeter may be perforated with thinner, break away regions of plastic. This arrangement facilitates separation of the sample receiving spot from the surrounding porous plastic through application of force to the sample receiving spot.

In another embodiment, cards are manufactured such that the perimeter of the sample receiving spot is somewhat thicker than the center of the sample receiving spot or the plastic material outside the perimeter. This arrangement facilitates containment of the applied sample to the desired location. The size and shape of a region of the card are pre determined by the design of the mold.

In yet another embodiment, cards are manufactured such that the perimeter of the sample receiving spot is somewhat thinner or weaker than the center of the sample receiving spot or the plastic material outside the perimeter of the sample receiving spot. This arrangement facilitates separation of the sample receiving spot from the surrounding porous plastic through application of force to the sample receiving spot. In one embodiment, the perimeter of the sample receiving spot may appear perforated, with discontinuities in the sintered porous plastic where a perforation occurs. These cards also contain a somewhat thicker region of plastic within the perimeter of the thinner or weaker zone. Such arrangement facilitates containment of the applied sample to the desired location and also facilitates separation of the sample receiving spot from the surrounding porous plastic through application of force to the sample receiving spot.

In another embodiment, cards are manufactured such that the sample receiving spot has a different hydrophobicity from non-sample receiving regions. In a specific embodiment, the sample receiving spot is hydrophilic and the non-sample receiving region is hydrophobic. The blood sample only wets and wicks into the hydrophilic sample receiving spot. The method of making regions of discrete hydrophobic and hydrophilic porous plastic is described in US Patent Application publication number US2003134100. Cards can be manufactured in the mold or by thermoforming. Thermoforming is a process of forming a profiled product from a flat sheet by applying heat and pressure to selected locations of flat sheet. In the present invention, in one embodiment, the flat sheet of sintered porous plastic is passed through a heated die with a profile that generates a desired pattern.

In another embodiment the card comprises sample receiving spots comprising a sintered porous plastic matrix and regions of non-porous plastic surrounding the sample receiving spots. In one embodiment, this card is made using an injection molding process with a hole that accommodates sintered porous plastic components, such as the sample receiving spot, channel or sample storage spot. These sintered porous plastic components are inset into the hole in the card. In another embodiment in which sample receiving spots are contained in a paper, cardboard, glass or non-porous plastic card, the sample receiving spots, and optionally channels and sample storage spots are made by sintering plastic to make a sintered porous plastic matrix. The sample receiving spots, and optionally channels and sample storage spots are then inserted into a preformed paper, cardboard, glass or non porous plastic card containing openings configured to accept the sample receiving spots, and optionally channels and sample storage spots. Such insertion may be accomplished through a frictional fit. In another embodiment, a preformed paper, cardboard, glass or non porous plastic card contains openings with flanges configured to accept the sample receiving spots, and optionally channels and sample storage spots.

Operation of the Card.

A liquid sample is applied to the card. In one embodiment, the sample requires that it is maintained in a wet state and the card is stored in a moist environment for subsequent use or transport, such as mailing. In another embodiment, the sample is permitted to dry. In one embodiment the card may then be stored for subsequent use or transport, such as mailing. Alternatively, after the sample dries, a portion of the card containing the sample may be obtained by cutting the card with a knife, scissors, a sharp punch of desired shape at the cutting surface, or another tool known to one of ordinary skill in the art. In another embodiment, the sample receiving spot may be punched away from the card by application of force to the sample receiving spot, especially in embodiments wherein the perimeter of the sample receiving spot is somewhat thinner or weaker that the plastic material on either side. When color change indicators are included in the sample receiving spot, the sharp punch of desired shape may be applied to the region of the sample receiving spot that changed color upon application of the liquid sample. At this point, several options exist. The cut portion of the sample receiving spot may be covered and stored until the appropriate time to perform a test on the sample contained therein. Alternatively, the cut portion of the sample receiving spot may be processed to perform a desired test to detect a selected analyte. In one embodiment, the cut portion of the sample receiving spot with a sharp edge may be treated with an ionic solution and then placed in a mass spectrometer for aerosolization of analytes on the sample receiving spot. The ionic solution can be any solution used for electrospray ionization, such as, a solution containing 5 mM ammonium bicarbonate and 100 mM ammonium acetate, pH=7.8. Other ionic solutions may be used as known to one of ordinary skill in the art. This aerosolization may be achieved through a variety of means such as applying a voltage to the sharp edge of the sample receiving spot fragment. When the sample receiving spot is polygonal in shape, for example triangular in shape, cutting the sample receiving spot may not be required as a sharp edge is provided upon punching the triangular sample receiving spot from the card. Then the corner of the triangular sample receiving spot may be treated with an ionic solution and then placed in a mass spectrometer for aerosolization of analytes on the sample receiving spot.

Alternatively, the sample receiving spot or a fragment thereof may be added to a receptacle such as a test tube, centrifuge tube or assay tube, and the sample may be processed, for example, by eluting the sample for assay of an analyte in the sample. The sample receiving spot or a fragment thereof may be cut or punched into a receptacle based on the card design and requirement. Such receptacles may also contain reagents useful in performing an assay of one or more analytes in the sample. Appropriate reagents are known to one of ordinary skill in the art and are chosen based on the analyte to be measured. For example, analyte-specific antibodies, optionally in addition to a colorimetric indicator may be used to bind to a protein and develop a color. In one embodiment, the sample may contain a protein or a peptide and the elution of the protein or a peptide from the spot or fragment thereof makes the protein or peptide available for measurement with an enzyme linked immunoabsorbent assay (ELISA) or radioimmunoassay (RIA). In another embodiment, the sample may contain another type of biological molecule, such as a lipid, a nucleic acid (for example DNA or RNA), or a neurotransmitter (such as catecholamines, indoleamines, acetylcholine) or metabolites thereof.

The sample card of the present invention can be used in a similar way described by GE Healthcare on their website (http://www.whatman.com) and in their literature concerning the cellulose-based GE DMPK FTA card. The sample card of the present invention has similar applications and can be used in similar ways as described in following US patents or patent applications: U.S. Pat. No. 6,627,226, US 2001/0000149, US 2007/0259445, U.S. Pat. Nos. 5,496,542, 5,756,126, 5,807,527, 5,985,327, 6,168,922, 6,447,804, 6,746,841, and 6,958,392.

Housing

The card may be used without a housing. The card has good mechanical strength, rigidity and can be used alone. Print can be applied to the card to indicate the company logo, to label the sample receiving spots, to label the type of card or other desired labels. A barcode and quick response (QR) code can be also directly printed onto the card. The card may also comprise a magnetic strip for information storage.

The card can be laminated to the other materials, such as cardboard or a plastic sheet using techniques familiar to one of ordinary skill in the art. The card can also be inserted into a frame sheet using techniques familiar to one of ordinary skill in the art.

The card may be placed in the appropriate storage conditions until the operator decides to perform the sample analysis. Cards may optionally contain a storage stabilizing agent, such as a desiccant or an oxygen scavenger. Cards may optionally be stored with a storage stabilizing agent, such as a desiccant or an oxygen scavenger.

Types of Samples

Liquid samples include but are not limited to biological and non-biological fluids. Biological fluids include, but are not limited to, bodily fluids such as blood, plasma, urine, peritoneal fluid, pulmonary fluid, pericardial fluid, tears, saliva, cerebrospinal fluid, lymphatic fluids, gastrointestinal fluids, feces, fluids of the reproductive system, and amniotic fluid. Other biological fluids include but are not limited to culture medium such as cell or tissue culture medium. Non-biological fluids include water samples including fresh water, sea water, and wastewater samples, organic solution samples, inorganic solution samples, samples from the petrochemical industry such as samples from oil fields, environmental samples and food samples. Biological and non-biological fluids may contain cells.

In one embodiment, when the biological sample is blood, the sample receiving spot may contain preservatives, chelating agents or chemicals useful in lysing cells and/or denaturing proteins, including enzymes. Samples also include but are not limited to tissues, animal or plant cells, microorganisms (for example, bacteria, viruses, mold, and fungi), and plasmids. Cells include, but are not limited to, cultured cells, epithelial cells, mesothelial cells, endothelial cells and stem cells or other progenitor cells. Cells may be obtained from tissues, organs and biological fluids using techniques known to one of ordinary skill in the art.

Target analytes include any desired analyte, such as nucleic acid (DNA, RNA), carbohydrates, lipids, proteins, peptides, hormones, antibodies, metabolites, neurotransmitters, immunomodulators, drugs, drug metabolites, alcohol, ions, or electrolytes. The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

EXAMPLE 1

Porous Plastic Card for Use in Delivery of Small Volume Blood Samples to an Assay A 100 gm young rat is injected with a drug and blood is sampled over time to examine the concentration of the drug and its metabolites in order to establish a pharmacokinetic and metabolic profile.

The rat is anesthetized and its tail vein is used to obtain a 10 µl sample of blood with a capillary tube. The 10 µl sample is applied to a sample receiving spot on a porous plastic card and dries. This sampling process continues every 30 min for 4 hours and each 10 µl sample is applied to a different sample receiving spot. The card containing the 10 µl blood samples is stored until a time selected for analysis.

Next, a sample of each blood spot is obtained using a punch with a circular shape. The punched circular region of the card containing the sample is then introduced into a centrifuge vial. A methanol solution is introduced into the vial to extract the drug metabolites. The clear solution is injected into a LC-MS in order to separate, detect and analyze the drug and its metabolites and establish a pharmacokinetic and metabolic profile.

EXAMPLE 2

Porous Plastic Card for Use in Delivery of Small Volume Blood Samples to a Mass Spectrometer A 100 gm young rat is injected with a drug and blood is sampled over time to examine the concentration of the drug and its metabolites in order to establish a pharmacokinetic and metabolic profile.

The rat is anesthetized and its tail vein is used to obtain a 10 µl sample of blood with a capillary tube. The 10 µl sample is applied to a sample receiving spot on a porous plastic card and dries. This sampling process continues every 30 min for 4 hours and each 10 µl sample is applied to a different sample receiving spot. The card containing the 10 µl blood samples is stored until a time selected for analysis.

Next, a sample of each blood spot is obtained using a punch with a triangular shape. The punched triangular region of the card containing the sample is then introduced into the mass spectrometer in order to detect and analyze the drug and its metabolites and establish a pharmacokinetic and metabolic profile.

EXAMPLE 3

Porous Plastic Card for Use in Forensic Pathology

A crime scene investigator arrives at a crime scene involving multiple blood spatters. The investigator uses a pipette to apply 5 µl samples of blood to individual sample receiving spots on a porous plastic card. Ultraviolet analysis of the crime scene reveals several samples of reproductive fluids which are collected and applied to sample receiving spots on another porous plastic card. The cards are stored until the laboratory is available for DNA analysis. A sample is eluted from each spot and the polymerase chain reaction is used for genomic analysis of DNA contained in white blood cells and in the reproductive fluids. The results are used to identify the crime victim and the perpetrator.

EXAMPLE 4

Multi-Channel Hydrophilic/Hydrophobic Porous Plastic Card for Use in Delivery of Small Volume Blood Samples to an Assay A 100 gm young rat is injected with a drug and blood is sampled over time to examine the concentration of the drug and its metabolites in order to establish a pharmacokinetic and metabolic profile.

Figure 5:
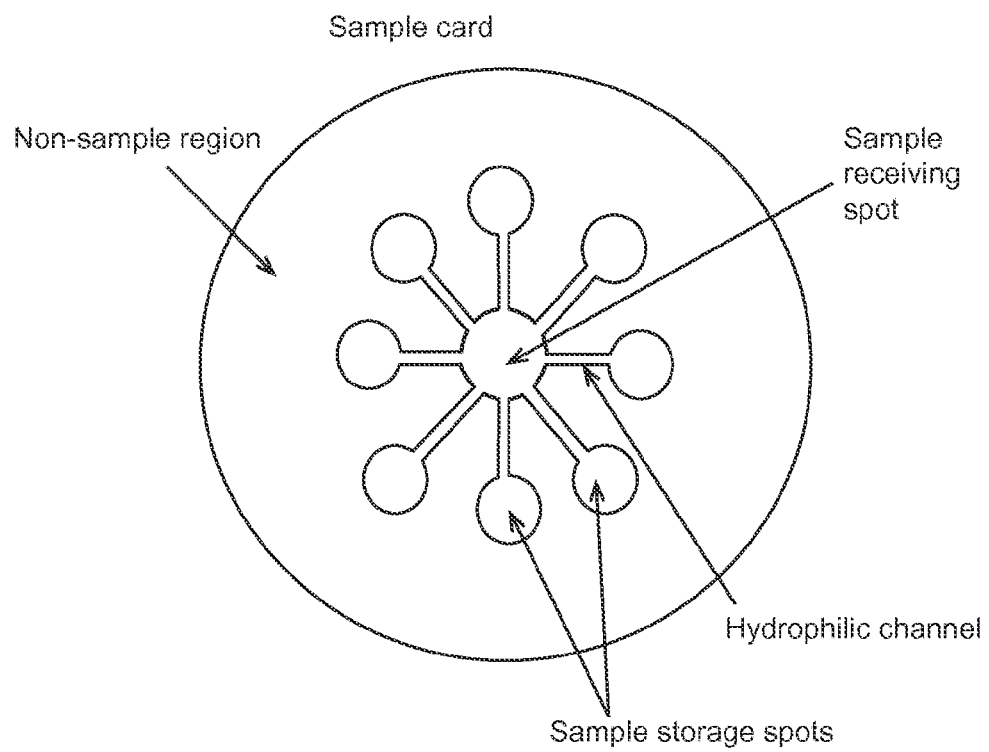
FIG. 5. Schematic representation of a hydrophilic-hydrophobic sample card. The center of the card contains a hydrophilic sample receiving spot connected by hydrophilic channels to hydrophilic sample storage spots all comprised of sintered porous plastic. The area of the card surrounding the hydrophilic sample receiving spot, the hydrophilic channels, and the hydrophilic sample storage spots is hydrophobic.
Figure 6:
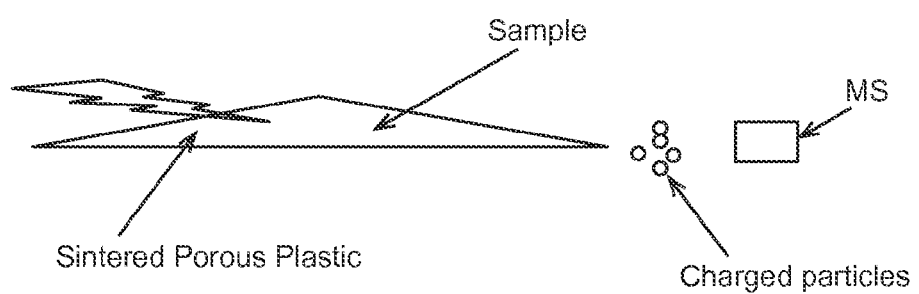
FIG. 6. Schematic representation of a sharp point of sintered porous plastic containing a sample. Following application of voltage, charged particles containing the sample are released from the sharp point and introduced into a mass spectrometer for analysis of selected analytes.
Figure 7:
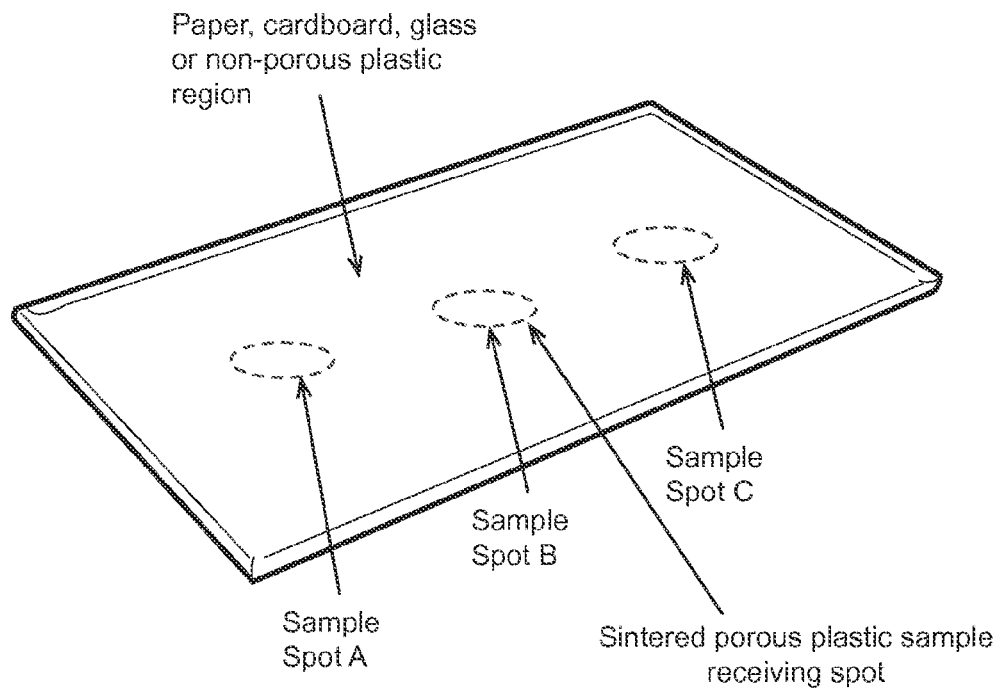
FIG. 7. Schematic representation of a sample card showing three sample spot receiving regions A, B, and C comprised of sintered porous plastic, surrounded by a region of the card comprised of paper, cardboard, glass or solid non-porous plastic that does not receive a sample. Each sample spot receiving region comprises a shallow region as the thickness of the card in the sample spot receiving region is less than the surrounding region of the card that does not receive a sample.

The rat is anesthetized and its tail vein is used to obtain a 100 µl sample of blood with a capillary tube. The 100 µl sample is applied to the sample receiving spot on a multi-channel hydrophilic-hydrophobic porous plastic card (FIG. 5). The blood wicks through the hydrophilic channels and reaches the sample storage spots. The card is dried. The card containing the 100 µl blood sample is stored until a time selected for analysis.

Next, a sample of blood from each sample storage spot is obtained using a punch with a circular shape. The punched circular region of the card containing the sample is then introduced into a centrifuge vial. Different storage spots may be punched into different vials for different assays or using different protocols. Some storage spots may be retained for future assays.

EXAMPLE 5

Sintered Porous Dry Blood Card

Powdered polyethylene having an average particle size of about 150 µm was disposed in a metal sheet (8"×11"×⅟16") mold, heated to 350° F. for about three minutes and subsequently cooled to room temperature in about five minutes. The sintered porous polyethylene sheet had an average pore size of about 30 µm and pore volume of about 40%.

EXAMPLE 6

Sintered Porous Dry Blood Card

Powdered UHMWPE polyethylene having an average particle size of about 30 µm was disposed in a metal sheet (8"×11"×⅟16") mold, heated to 350° F. for about three minutes and subsequently cooled to room temperature in about five minutes. The sintered porous UHMWPE sheet had an average pore size of about 10 µm and pore volume of about 40%.

EXAMPLE 7

Sintered Porous Dry Blood Card

Powdered high density polyethylene (HDPE) having an average particle size of about 300 μm was disposed in a metal sheet (8"×11"×1/16") mold, heated to 350° F. for about three minutes and subsequently cooled to room temperature in about five minutes. The sintered porous HDPE sheet had an average pore size of about 80 μm and pore volume of about 40%.

EXAMPLE 8

Sintered Porous Dry Blood Card

Powdered polystyrene having an average particle size of about 180 μm was disposed in a metal sheet (8"×11"×1/16") mold, heated to 370° F. for about three minutes and subsequently cooled to room temperature in about five minutes. The sintered porous polyethylene sheet had an average pore size of about 45 μm and pore volume of about 40%.

EXAMPLE 9

Hydrophilic Sintered Porous Dry Blood Card

Sintered porous dry blood cards from examples 5-8 were treated with low pressure plasma. The sample cards were treated with oxygen plasma at 100 mtorr and 100 watts (W) for 10 minutes in a plasma machine (Europlasma, Oudenaards, Belgium). The cards became hydrophilic and adsorbed 20 μl deionized water in less than 3 seconds when 20 μl deionized water was placed on top of the cards with a pipette.

EXAMPLE 10

Hydrophilic Sintered Porous Dry Blood Card

Sintered porous dry blood cards from examples 5-8 were treated with surfactants. The sample cards were immersed in a solution comprises of 79% deionized water, 20% isopropyl alcohol and 1% Tween® 20 at room temperature for 12 hours and dried at 70° F. for 8 hours in an oven. The cards became hydrophilic and adsorbed 20 μl deionized water in less than 3 seconds when 20 μl deionized water was placed on top of the cards with a pipette.

EXAMPLE 11

Sintered Hydrophilic Porous Dry Blood Card comprising Dry Anionic Surfactant

A powdered mixture comprising 99.5% of polyethylene powders having an average particle size of about 150 μm and 0.5% of sodium dodecyl sulfate (SDS) was disposed in a metal sheet (8"×11"×1/16") mold, heated to 350° F. for about three minutes and subsequently cooled to room temperature in about five minutes. The resulting sintered porous polyethylene sheet had an average pore size of about 30 μm and pore volume of about 40%. The cards were hydrophilic and adsorbed 20 μl deionized water in less than 3 seconds when 20 μl deionized water was placed on top of the cards with a pipette.

EXAMPLE 12

Sintered Hydrophilic Porous Dry Blood Card comprising Dry Anionic Surfactant

A powdered mixture comprising 99.5% of UHMWPE polyethylene having an average particle size of about 30 μm and 0.5% of sodium dodecyl sulfate (SDS) powder is disposed in a metal sheet (8"×11"×1/16") mold and is heated to 350° F. for about three minutes and subsequently is cooled to room temperature in about five minutes. The resulting sintered porous UHMWPE sheet has an average pore size of about 10 μm and pore volume of about 40%. The cards are hydrophilic and adsorb 20 μl deionized water in less than 3 seconds when 20 μl deionized water is placed on top of the cards with a pipette.

EXAMPLE 13

Sintered Hydrophilic Porous Dry Blood Card comprising Dry Cationic Surfactant

A powdered mixture comprising 99% of polyethylene powders having an average particle size of about 150 μm and 1% of cetyltrimethylammonium bromide (CTAB) is disposed in a metal sheet (8"×11"×1/16") mold, heated to 350° F. for about three minutes and subsequently cooled to room temperature in about five minutes. The resulting sintered porous polyethylene sheet has an average pore size of about 30 μm and pore volume of about 40%. The cards are hydrophilic and adsorb 20 μl deionized water in less than 3 seconds when 20 μl deionized water is placed on top of the cards with a pipette.

EXAMPLE 14

Sintered Hydrophilic Porous Dry Blood Card comprising Dry Cationic Surfactant

A powdered mixture comprising 99% of UHMWPE polyethylene having an average particle size of about 30 μm and 1% of cetyltrimethylammonium bromide (CTAB) is disposed in a metal sheet (8"×11"×1/16") mold, heated to 350° F. for about three minutes and subsequently cooled to room temperature in about five minutes. The resulting sintered porous polyethylene sheet has an average pore size of about 10 μm and pore volume of about 40%. The cards are hydrophilic and adsorb 20 μl deionized water in less than 3 seconds when 20 μl deionized water is placed on top of the cards with a pipette.

EXAMPLE 15

Hydrophilic Sintered Porous Dry Blood Card with Multilayer Polyelectrolyte Coating Sintered porous dry blood cards from example 9 were further treated with an polyelectrolyte solution to improve hydrophilic stability. The freshly plasma treated sample cards were immersed in 0.25% polyethylenimine (750 KDa) water-alcohol solution (80% deionized water and 20% isopropyl alcohol) at room temperature for 10 minutes, dried at 50° F. for 10 minutes in an oven, immersed in 0.25% polyacrylic acid (250 KDa) water-alcohol solution (80% deionized water and 20% isopropyl alcohol) at room temperature for 10 minutes and dried at 50° F. for 10 minutes. The cards were hydrophilic and adsorbed 20 μl deionized water in less than 3 seconds when 20 μl deionized water was placed on top of the cards with a pipette.

EXAMPLE 16

Hydrophilic Sintered Porous Dry Blood Card with Polyelectrolyte and Surfactant Coating Sintered porous dry blood cards from example 9 were further treated with polyelectrolyte solution to improve hydrophilic stability. The freshly plasma treated sample cards were immersed in 0.25% polyethylenimine (750 KDa) water-alcohol solution (80% deionized water and 20% isopropyl alcohol) at room temperature for 10 minutes, dried at 50 degree for 10 minutes in an oven, immersed in 0.1% Zonyl® FSK water-alcohol solution (80% deionized water and 20% isopropyl alcohol) at room temperature for 10 minutes and dried at 50° F. for 10 minutes. The cards were hydrophilic and adsorbed 20 μl deionized water in less than 3 seconds when 20 μl deionized water was placed on top of the cards with a pipette.

EXAMPLE 17

Hydrophilic Sintered Porous Dry Blood Card with Heparin

Sintered porous dry blood cards from examples 5-8 are treated with surfactant and heparin. The sample cards are immersed in a water-isopropyl alcohol solution (80:20) comprising 1% Tween® 20 and 0.5% heparin sodium salt at room temperature for 12 hours and dried at 70° F. for 8 hours in an oven. The cards become hydrophilic and adsorb 20 μl deionized water in less than 3 seconds when 20 μl deionized water is placed on top of the cards with a pipette.

EXAMPLE 18

Hydrophilic Sintered Porous Dry Blood Card with Polyelectrolyte and Heparin Coating Sintered porous dry blood cards from example 9 are further treated with polyelectrolyte solution and heparin solution to improve blood compatibility. The freshly plasma treated sample cards are immersed in 0.25% polyethylenimine (750 KDa) water-alcohol solution (80% deionized water: 20% isopropyl alcohol) at room temperature for 10 minutes, dried at 50° F. for 10 minutes in an oven and then immersed in 0.1% heparin sodium salt water solution (80% deionized water: 20% isopropyl alcohol) at room temperature for 10 minutes and dried at 50° F. for 10 minutes The cards are hydrophilic and adsorb 20 μl deionized water in less than 3 seconds when 20 μl deionized water is placed on top of the cards with a pipette.

EXAMPLE 19

Sintered Hydrophilic Porous Dry Blood Card comprising C-18 Silica Gel

A powdered mixture comprising 70% of UHMWPE polyethylene having an average particle size of about 30 μm and 30% of C-18 silica gel with average particle size of 30 μm is disposed in a metal sheet (8"×11"×1/16") mold, heated to 350° F. for about three minutes and subsequently cooled to room temperature in about five minutes. The sintered porous composite sheet has an average pore size of about 10 μm and pore volume of about 40%. The cards are optionally further treated with surfactant solution to provide hydrophilicity.

EXAMPLE 20

Sintered Hydrophilic Porous Dry Blood Card comprising Ion Exchange Resins

A powdered mixture comprising 70% of UHMWPE polyethylene having an average particle size of about 30 μm and 30% of Dowex® 50WX2 fine mesh resin (200 to 400 meshes) with average particle size of 50 μm is disposed in a metal sheet (8"×11"×1/16") mold, heated to 350° F. for about three minutes and subsequently cooled to room temperature in about five minutes. The sintered porous composite sheet has an average pore size of about 12 μm and pore volume of about 40%. The cards are optionally further treated with surfactant solution to provide hydrophilicity.

EXAMPLE 21

Sintered Hydrophilic Porous Dry Blood Card comprising Chelating Agents

A powdered mixture comprising 95% of UHMWPE polyethylene having an average particle size of about 30 μm and 5% of ethylenediaminetetraacetic acid (EDTA) powder with average particle size of 50 μm is disposed in a metal sheet (8"×11"×1/16") mold, heated to 350° F. for about three minutes and subsequently cooled to room temperature in about five minutes. The sintered porous composite sheet has an average pore size of about 10 μm and pore volume of about 40%. The cards are optionally further treated with surfactant solution to provide hydrophilicity.

EXAMPLE 22

Sintered Hydrophilic Porous Dry Blood Card comprising DNA Stabilizing Agents

A powdered mixture comprising 98% of UHMWPE polyethylene having an average particle size of about 30 μm and 2% of uric acid powder with average particle size of 50 μm is disposed in a metal sheet (8"×11"×1/16") mold, heated to 350° F. for about three minutes and subsequently cooled to room temperature in about five minutes. The sintered porous composite sheet has an average pore size of about 10 μm and pore volume of about 40%. The cards are optionally further treated with surfactant solution to provide hydrophilicity.

EXAMPLE 23

Sintered Hydrophilic Porous Dry Blood Card comprising Chaotropic Agents

A powdered mixture comprising 98% of UHMWPE polyethylene having an average particle size of about 30 μm and 2% of guanidinium chloride powder with average particle size of 50 μm is disposed in a metal sheet (8"×11"×1/16") mold, heated to 350° F. for about three minutes and subsequently cooled to room temperature in about five minutes. The sintered porous composite sheet has an average pore size of about 10 μm and pore volume of about 40%. The cards are optionally further treated with surfactant solution to provide hydrophilicity.

EXAMPLE 24

Sintered Hydrophilic Porous Dry Blood Card comprising Multiple Additives for Blood Preservation A powdered mixture comprising 90% of UHMWPE polyethylene having an average particle size of about 30 μm and 2% of uric acid powder with average particle size of 50 μm, 2% of guanidinium chloride powder with average particle size of 50 μm, 5% of ethylenediaminetetraacetic acid (EDTA) powder with average particle size of 50 μm and 1% of sodium dodecyl sulfate (SDS) powder is disposed in a metal sheet (8"×11"×1/16") mold, heated to 350° F. for about three minutes and subsequently cooled to room temperature in about five minutes. The sintered porous composite sheet has an average pore size of about 12 μm and pore volume of about 40%. The cards are hydrophilic and adsorb 20 μl deionized water in less than 3 seconds when 20 μl deionized water is placed on top of the cards with a pipette.

EXAMPLE 25

Recovery of Caffeine from Sintered Hydrophilic Porous Cards

Three hydrophilic sintered polyethylene sheets were selected for test sampling properties. The sheets had different pore sizes (100 µm, 50 µm, and 8 µm) with thicknesses of 1.6 mm, 1.6 mm and 0.25 mm, respectively, as shown in Tables 1 and 2. The 100 µm sheet comprised 0.2% of the anionic surfactant sodium N-methyl-N-oleoyltaurate. The 50 µm sheet comprised 0.2% of the anionic surfactant sodium N-methyl-N-oleoyltaurate. The percentage of the surfactant is the blended weight percentage before sintering. The 8 µm sheet was treated with plasma activation and sequentially treated with an aqueous solution of 0.25% polyethylenimine an aqueous solution of 0.25% poly(acrylic acid).

Figure 8:
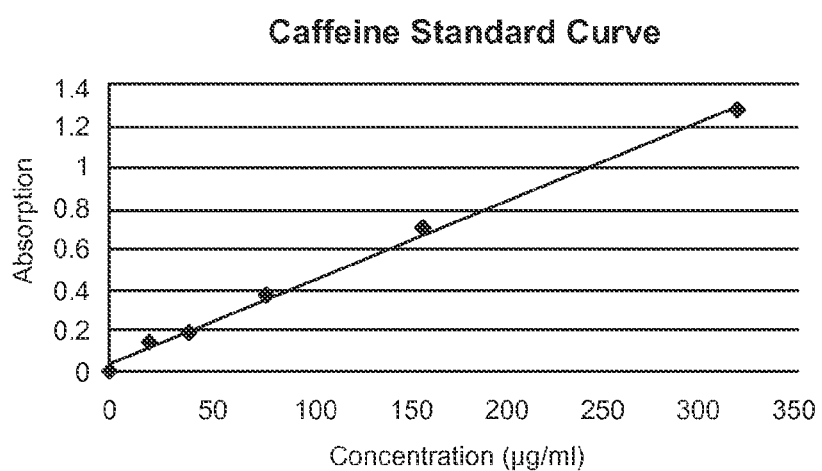
FIG. 8. Standard curve of UV Absorption for serial dilution of caffeine in water.

Artificial plasma was formulated with phosphate buffer, red food dye, bovine serum albumin and sodium azide. Caffeine was obtained from Sigma Aldrich. Caffeine was mixed with artificial plasma to form a 10 mg/ml solution. A caffeine standard solution (10 mg caffeine/ml) was made and serially diluted in deionized water solution. The standard UV absorption curve for these serially diluted caffeine solutions is show in FIG. 8. The UV absorption was measured on a Thermo-Fisher NanoDrop 2000 machine. The caffeine was measured at the wavelength of 273 nm. The wavelength selection was based on the caffeine UV absorption curve and the UV absorption curve for artificial plasma.

20 µl of artificial plasma was pipetted onto each hydrophilic sheet. The different sheets had clearly visible differences in sample spot diameters as indicated in Table 1. Properties of the sheet samples are list in Table 1. These samples were used as a background measurement in order to measure caffeine samples.

TABLE 1

Artificial plasma spot on the card samples.

| Porex Sheets | Sample size (µl) | Spot diameter (mm) | Thickness (mm) |
|---|---|---|---|
| 100 µm | 20 | 6 | 1.6 |
| 50 µm | 20 | 8 | 1.6 |
| 8 µm | 20 | 18 | 0.25 |

20 µl of artificial plasma containing 10 mg/ml caffeine (total of 200 µg caffeine) was pipetted onto separate sheet samples with the same properties. The samples were dried at room temperature for 2 hours. Then sample spots were punched with a 6 mm diameter paper punch. The resulting 6 mm diameter disks were separately transferred into 7 ml glass vials. The samples in the vials were extracted with 1 ml deionized water for 2 hours. The UV absorption of these aqueous extracts were measured for the samples with artificial plasma and the samples with caffeine in the artificial plasma. The difference for the same sample with and without caffeine was measured for caffeine released from the sampling cards. The readings were estimated to the closest 5 µg/ml using the caffeine deionized water standard curve. The results in Table 2 show caffeine recoveries of 65% to 87.5%.

TABLE 2

Caffeine recovery from Porex sheets.

| Porex Sheets | UV Absorption (273 nm) | Factor (punch size) | Measured Caffeine Concentration (µg) | Recovery % |
|---|---|---|---|---|
| 100 µm | 0.77 | 1 | 175 | 87.5 |
| 50 µm | 0.35 | 1.78 | 150 | 75 |
| 8 µm | 0.065 | 9 | 130 | 65 |

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

The invention claimed is:

1. A card for receiving a liquid sample, the card comprising:
   (a) at least one sintered porous plastic liquid sample receiving spot; and
   (b) a non-porous non-sample receiving region surrounding the at least one liquid sample receiving spot, the non-porous non-sample receiving region comprising at least one opening through the card and into which the at least one sintered porous plastic sample receiving spot is configured to be inserted, wherein the liquid sample receiving spot is configured to be removed from the non-sample receiving portion upon application of force to the liquid sample receiving spot.

2. The card of claim 1, wherein the sintered porous plastic comprises a plastic selected from the group consisting of polyethylene, polypropylene, polyvinylidene fluoride, polyamide, polyacrylate, polyacrylic nitrile, ethylene-vinyl acetate, polyester, polycarbonate, polystyrene, and polytetrafluoroethylene or a blend thereof.

3. The card of claim 2, wherein the polyethylene is selected from the group consisting of high density polyethylene, low density polyethylene and ultra high molecular weight polyethylene, or a blend thereof.

4. The card of claim 1, wherein the at least one liquid sample receiving spot is hydrophilic.

5. The card of claim 1, wherein the at least one liquid sample receiving spot is suitable for introduction into a mass spectrometer.

6. The card of claim 1, wherein the at least one liquid sample receiving spot further comprises a functional additive.

7. The functional additive of claim 6, wherein the functional additive is a color change indicator, a surfactant, a chelating agent, an anti-clotting agent, a polyelectrolyte, an enzyme inhibitor, a cell lysing reagent, an antioxidant, a DNA stabilizing agent, or a chaotropic agent or a combination thereof.

8. The card of claim 1, wherein the non-porous region surrounding the at least one liquid sample receiving spot comprises non-porous plastic or glass.

9. The card of claim 1, wherein the at least one sintered porous plastic sample receiving spot comprises a porosity of from about 20% to about 80%, from about 25% to about 70%, from about 30% to about 60%, or from about 30% to about 50%.

10. The card of claim 1, wherein the at least one sintered porous plastic sample receiving spot comprises a pore size of from about 1 µm to about 200 µm, from about 10 µm to about 100 µm, or from about 20 µm to about 60 µm.

11. The card of claim 1, wherein the at least one sintered porous plastic sample receiving spot comprises a thickness of up to about 3 mm.

12. The card of claim 1, wherein the region surrounding the liquid sample receiving spot has a region to accept labeling, writing, a barcode, a QR code, a magnetic strip, or a combination thereof.

13. A method for liquid sample collection, storage, transport, and/or delivery to an analytical device comprising:
providing a card comprising at least one sintered porous plastic liquid sample receiving spot and a non-porous region surrounding the at least one liquid sample receiving spot; the non-porous non-sample receiving region comprising at least one opening into which the at least one sintered porous plastic sample receiving spot is configured to be positioned such that the entire liquid sample receiving spot is configured to be punched away from the card by application of force to the liquid sample receiving spot;
applying a liquid sample to the at least one liquid sample receiving spot;
allowing the liquid sample to be absorbed by the liquid sample receiving spot by capillary force;
removing the at least one liquid sample receiving spot from the card by application of force to the liquid sample receiving spot;
transporting or delivering the liquid sample receiving spot to an analytical device.

14. The method of claim 13 comprising permitting the liquid sample to dry after applying the liquid sample to the at least one liquid sample receiving spot.

15. The method of claim 13, wherein the liquid sample is a biological fluid or a non-biological fluid.

16. The method of claim 15, wherein the biological fluid comprises blood, plasma, urine, peritoneal fluid, pulmonary fluid, pericardial fluid, tears, saliva, cerebrospinal fluid, lymphatic fluid, gastrointestinal fluid, feces, a fluid of the reproductive system, amniotic fluid, culture medium, cells, microorganisms or plasmids.

17. The method of claim 13, further comprising eluting the sample from the at least one liquid sample receiving spot.

18. A card for receiving a liquid sample, the card comprising
(a) at least one liquid sample receiving spot comprised of a sintered porous plastic matrix; and
(b) a non-porous non-sample receiving region forming a card body and comprising at least one opening formed therethrough configured for surrounding the at least one liquid sample receiving spot, wherein the at least one liquid sample receiving spot is configured to be inserted into the opening via frictional fit.

19. A card for receiving a liquid sample, the card comprising
(a) a non-porous non-sample receiving region forming a card body having one or more openings formed through the card body;
(b) one or more sintered porous plastic liquid sample receiving spots received by the one or more openings, wherein the one or more liquid sample receiving spots are configured to (i) receive a sample, (ii) allow the sample to dry on the spot, and (iii) be punched away from the card by application of force for analysis of the sample.

* * * * *